United States Patent [19]

Kummer

[11] Patent Number: 5,163,948
[45] Date of Patent: Nov. 17, 1992

[54] NERVE TISSUE REPAIR APPARATUS AND METHOD

[75] Inventor: Frederick J. Kummer, Brooklyn, N.Y.

[73] Assignee: Hospital for Joint Diseases, New York, N.Y.

[21] Appl. No.: 694,756

[22] Filed: May 2, 1991

[51] Int. Cl.⁵ .............................................. A61B 17/00
[52] U.S. Cl. ...................................... 606/152; 606/151
[58] Field of Search ............. 606/152, 146, 151, 103, 606/121, 122, 124, 108; 242/310, 250, 243; 43/44.98, 18.1

[56] References Cited

U.S. PATENT DOCUMENTS

| | | | |
|---|---|---|---|
| 745,992 | 12/1903 | Bargeboer | 606/124 |
| 1,326,800 | 12/1919 | Spruyt | 606/124 |
| 3,556,427 | 1/1971 | Lemery et al. | 242/310 X |
| 4,145,028 | 3/1979 | Kelly et al. | 254/380 X |
| 4,863,469 | 9/1989 | Van Beek et al. | 623/8 |
| 4,890,615 | 1/1990 | Caspari et al. | 606/146 |
| 4,935,027 | 6/1990 | Yoon | 606/146 |

Primary Examiner—Stephen C. Pellegrino
Assistant Examiner—Jeffrey A. Schmidt
Attorney, Agent, or Firm—Stephen E. Feldman

[57] ABSTRACT

A windlass is mounted in fixed position external to the body and close to the nerve tissue to be lengthened. A first path in the form of a hollow member is made between the windlass and a second path, along which the nerve tissue is to be extended. A line is connected to the rotatable drum of the windlass and is passed along the first path and the second path to the nerve tissue. The line is connected by a protective cap to the nerve tissue. The drum is rotated, winding the line about the drum and drawing the line through the first and second paths while drawing the nerve tissue along the second path.

18 Claims, 2 Drawing Sheets

NERVE TISSUE REPAIR APPARATUS AND METHOD

BACKGROUND OF THE INVENTION

1. Field of the Invention

The present invention relates to apparatus and methods for connecting and repairing severed and separated nerve tissue. In particular, the present invention is directed to an apparatus and method for bringing together and joining the ends or stumps of nerve tissue where the nerve tissue has been severed, with the served ends of the nerve tissue spaced or gapped.

2. Prior Art

The repair of severed and/or broken nerve tissue has been addressed in the prior art. U.S. Pat. No. 3,786,817, issued to Palma teaches the joining of the ends of severed nerve tissue by inserting the severed ends in opposite ends of a tube so that the ends of the nerve tissue may be joined and begin growing together or regenerating. An opening in the tube provides for injection of matter for generating a environment conducive to nerve regeneration. After the nerve tissue ends have rejoined, the tube is removed from around the nerve junction by rupturing the tube.

The apparatus disclosed in this patent has several disadvantages. It is known that when nerve tissue is separated by a blow or striking force some of the nerve tissue adjacent the separated ends is damaged or destroyed, leaving a gap or spacing between the ends of the tissue. This gap or spacing between the ends of the severed nerve tissue must be overcome by lengthening the nerve tissue before the nerve ends can be physically joined, and the '817 patent does not address this problem. Another disadvantage is that after the nerve tissue has been lengthened the nerve tissue ends must be inserted in opposite ends of a tube and the person inserting the nerve ends into the tube does not have visual contact with the nerve ends when the ends are inside the tube. Without visual contact with the nerve ends, it is difficult to determine when the nerve ends are physically rejoined inside the tube. The teaching does not allow for the suturing of the nerve tissue ends, the nerve tissue ends are left to just grow together at will. Approximation, i.e., suturing, the nerve ends together more positively aligns the tissue and promotes healing of the severed tissue. Another problem inherent in this teaching is that the tube into which the nerve ends are inserted must be removed from around the nerve after regeneration of the nerve tissue occurs. Removal of the tube requires that the flesh be opened and that the tube be removed from around the nerve tissue. Palma overcomes this last problem in his U.S. Pat. No. 3,833,002 in which he discloses the use of a tubing made from a slow-dissolving material. However, the '002 patent fails to address other problems in the '817 patent.

The problem of visual contact with the ends of separated nerve tissue is addressed by de Medinaceli in his U.S. Pat. No. 4,586,504. This patent discloses a foldable sheet which is pre-marked, on which the nerve stumps are positioned while the sheet is open, according visual contact with the nerve tissue ends. The problem in the '504 patent is that this teaching does not address the problem of nerve end gap or spacing.

U.S. Pat. No. 4,662,884 issued to Stensaas, et al, discloses a nerve prostheses for promoting nerve tissue regeneration where there is no gap or very little gap between the severed nerve ends and suggests nerve tissue graft where the gap between nerve ends is 1 to 2 centimeters, or more. The severed nerve ends are brought together and held inside a tubular prostheses. However, after rejoining of the nerve tissue ends occurs, the tubular prostheses must be removed from around the nerve by opening the flesh. U.S. Pat. No. 4,863,469, issued to Van Beek, et al, discloses a nerve tissue expander for lengthening damaged nerve tissue. The apparatus taught in the '469 patent includes a saddle trough attached to an expandable or inflatable plate. The inflatable plate and saddle trough are inserted into the flesh, under the nerve tissue, and the nerve tissue is secured in the saddle trough. The inflatable plate is expanded over a time period thereby lengthening the nerve tissue to overcome any gap that may have occurred in the nerve tissue. This apparatus is bulky and cumbersome and the apparatus must be removed from the body by operative procedure after the nerve tissue has been regenerated.

SUMMARY OF THE INVENTION

The present invention overcomes the disadvantages of the prior art where nerve tissue lengthening and repair is concerned. The present invention addresses the problem attendant the lengthening of nerve tissue where a spacing or a gap has been developed between severed nerve tissue ends and has overcome the problem of removing the nerve lengthening apparatus from the body after the nerve tissue has been lengthened and of removing the nerve aligning apparatus used to hold the nerve ends together after the nerve tissue ends or stumps have become physically connected or rejoined. The present invention is unique over the prior art in that the main mechanical element of the apparatus is external to the body and the vehicle used to lengthen the nerve tissue is self-removing from the body, during the lengthening process. When the invention is practiced to lengthen nerve tissue and/or close a spacing or gap between severed nerve ends, the come-along apparatus in contact with the stump of the nerve tissue being lengthened is being removed from the body as the nerve tissue is being lengthened. This avoids the need for operative procedure to remove apparatus previously inserted into the body to effect nerve tissue lengthening.

Reduction of the spacing or gap between the nerve tissue ends or stumps in accomplished by use of an external windlass mounted on a bar or block, the bar being stabilized relative to the nerve on which repair is to be accomplished. The bar carrying the windlass may for example, be mounted on bone material in the area of the nerve tissue break, being held in an offset position by mounting the bar on the shafts of screws or pins set in the bone matter. A hollow tube, hollow shaft or hollow needle, (hereinafter referred to as needle or hollow needle), is passed through the bar or block and preferably into the bone, forming a fixed path between the upper surface of the block and the level of a latent path in the body along which one end, the proximal end of the severed nerve will be drawn. The sharp end of the hollow needle may be driven into the bone in order to stabilize the position of the needle, to stabilize the fixed path through the needle and the needle may serve to point to or locate one of the ends of the severed nerve, for example the distal end of the nerve tissue. The needle is sufficiently long so as to extend to or slightly above the upper surface of the bar, where the windlass is secured. The hollow needle is held in the bar or block by, for example, a set screw. With the location of the distal end of the severed nerve tissue pointed out by the needle the other end, the proximal end, of the nerve tissue is secured to a cable, line or wire (hereinafter referred to as wire or line) by means of attaching the proximal end of the nerve tissue to a protective cone. The cone is connected to one end of the wire. The wire is laid, fed or snaked through the body between the proximal end of the nerve and the lower, open end of the hollow needle forming a latent path through the body for the nerve tissue. The hollow needle, at its lower end, has an opening into the hollow chamber of the needle, which chamber has a second opening at the top end of the needle. The wire follows from the latent path, in the flesh, into the lower needle opening, through the fixed path formed by the hollow needle chamber to the top of the needle and out the top of the needle, at the upper surface of the bar or block. The wire is then connected to the drum of the windlass, to be wound around the drum as the drum rotates.

Thus connected, the drum or shaft of the windlass is rotated very slowly taking up the wire as the drum rotates. Rotation of the drum pulls the wire and attached protective cone and attached nerve through the path made by the wire toward the lower opening in the needle.

The windlass may be manually rotated and may include a ratchet mechanism or may be rotated be a motor drive, preferably a stepping motor, which will rotate the drum incrementally, very slowly. As the drum of the windlass is rotated, the wire is wound around the drum, pulling the wire along the fixed path and along the latent path. The protective cone, which is attached to the wire and to which the proximal end of the nerve is attached, becomes a come-along, pulling the nerve tissue along the path made by the wire/cone combination. When practicing the invention, lengthening of the nerve tissue to overcome a spacing or gap may be done very slowly, for example, at a rate which approaches 0.5 to 1.0 mm per day, or what ever increase in length the nerve tissue is capable of accepting. As the nerve tissue is lengthened, the gap or spacing between the distal end and the advancing proximal end is reduced. During the lengthening process, the vehicle used to accomplish such reduction in the gap is being removed from the flesh, in which it was previously laid.

When the proximal end portion of the nerve tissue is lengthened so that the proximal end and the distal end of the nerve tissue may be rejoined, the protective cone may be removed from the proximal end of the nerve and the nerve ends may be joined.

Preferably the hollow needle will be positioned somewhat up the nerve tissue from the distal end so that the proximal end may be lengthened to an overlapping position so that the protective cone may be removed from the proximal end and the tissue ends may be joined. Preferably, the nerve ends are sutured so that regeneration or rejoining of the nerve tissue may occur, as desired.

The hollow needle citing the distal end of the nerve tissue is removed and the bar and screws holding the bar to the bone are removed.

In practicing the invention, the physical rejoining of the severed nerve tissue, for regenerative purposes, may take any of several forms. Some prior art techniques for combining the nerve stumps may be used although suturing the nerve end together, end to end, is preferred.

DETAILED DESCRIPTION OF THE INVENTION

It should be understood that although the preferred embodiment and an alternate embodiment of the invention are represented and described, the invention is not limited to the described embodiments.

Figure 1:
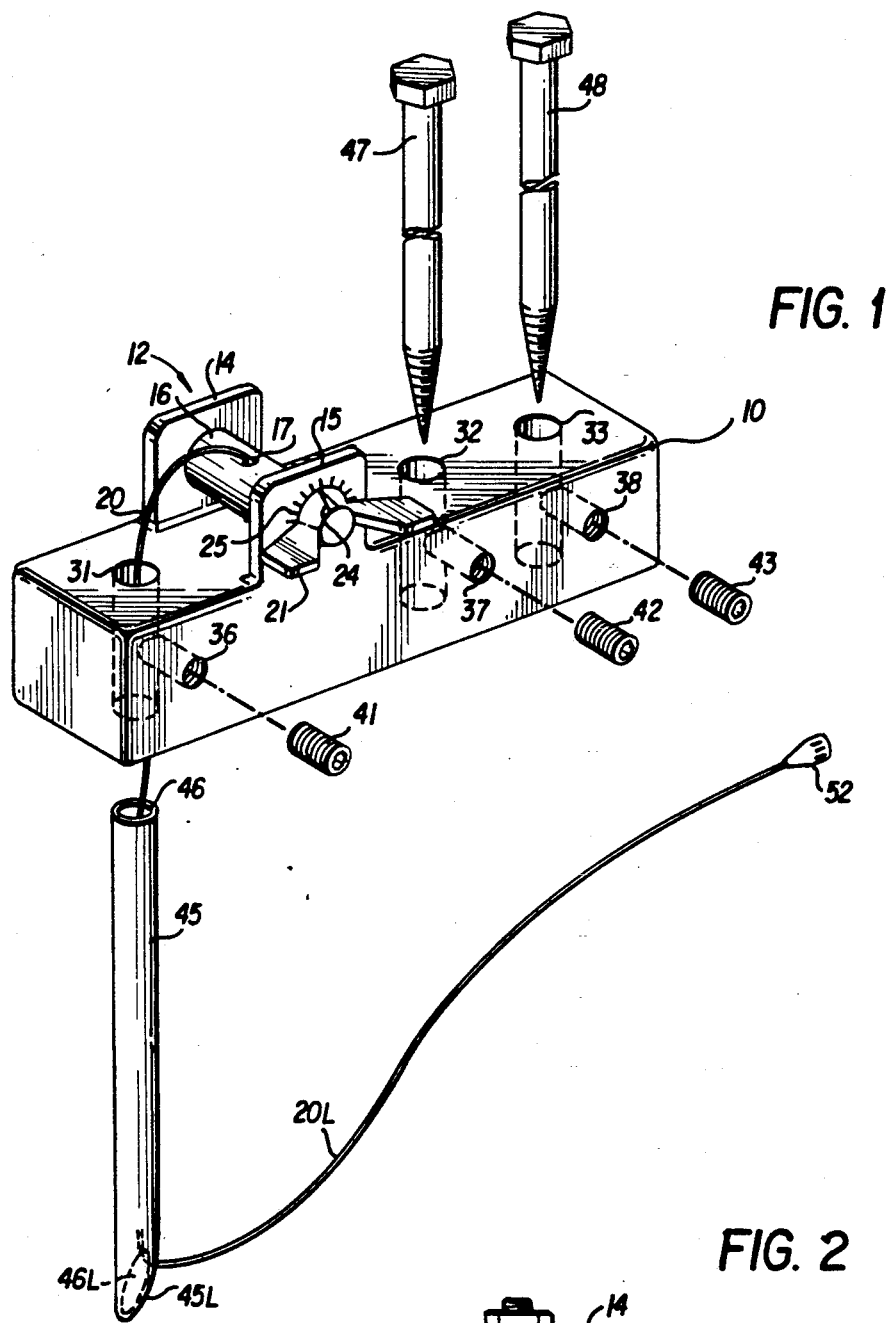
FIG. 1 is a pictorial representation of the invention in perspective, exploded view.

The invention represented in FIG. 1 shows a bar or block 10 on which is mounted, on its top, a windlass 12. The flanges 14 and 15 support a drum or barrel 16 which is mounted in the flanges so that the drum may be rotated in its mounting. The barrel includes hole 17 through which a wire 20 may be inserted to secure the wire to the barrel or drum and prevent slippage of the wire. The wire 20 represents a wire, cable, cord or line, suitable for temporary implant, made of any material acceptable for insertion and use in the body. Although stainless steel wire is preferred, other metal and/or materials such as plastic for example, may be used, as desired.

A wing member 21 is connected to the drum or shaft or barrel 16 so that the drum 16 may be rotated within its mounting, so as to take-up the wire 20. The wing member may include an indicator 24 and the windlass assembly may also include a calibration 25 so that one may know how much of the wire is taken-up by the drum, as the drum is rotated. The calibration scale would depend upon the diameter of the drum.

The block or bar 10 includes three holes 31, 32 and 33 that define shafts running from the top surface to the bottom surface of block 10. Each shaft includes a set screw shaft, 36, 37 and 38 each of which exits on the side of the block and communicates with the shafts with which the set screw shaft is associated. Each set screw shaft is tapped with threads to accept a threaded set screw, such as 41, 42 and 43, respectively.

A hollow needle 45 is of a diameter so that the needle will fit snugly in the shaft 31 and yet slide freely in the shaft. The set screw 41 is used to secure a vertical position of the needle 45 in the shaft 31. To secure and hold a vertical position of the needle 45 in the shaft 31, the set screw 41 is screwed into the set screw shaft 36 until the set screw impinges upon needle, driving the needle against the wall of the shaft 31 thus holding the needle in a desired vertical position in the block or bar 10.

Figure 2:
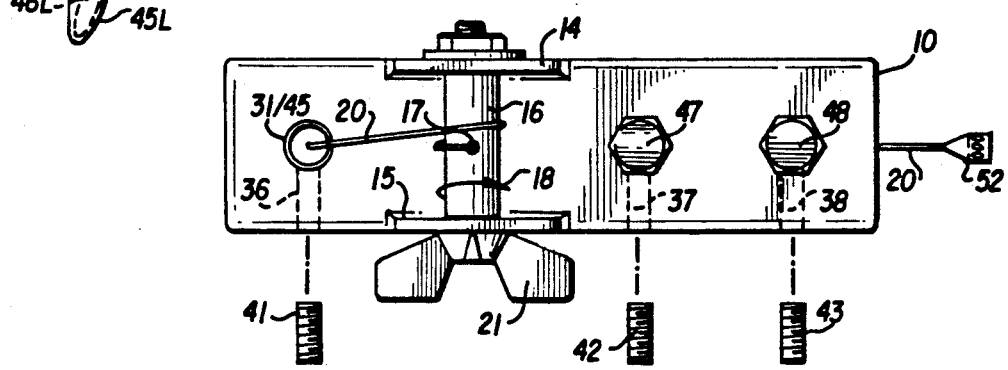
FIG. 2 is a representation of the invention, in plan view.
Figure 3:
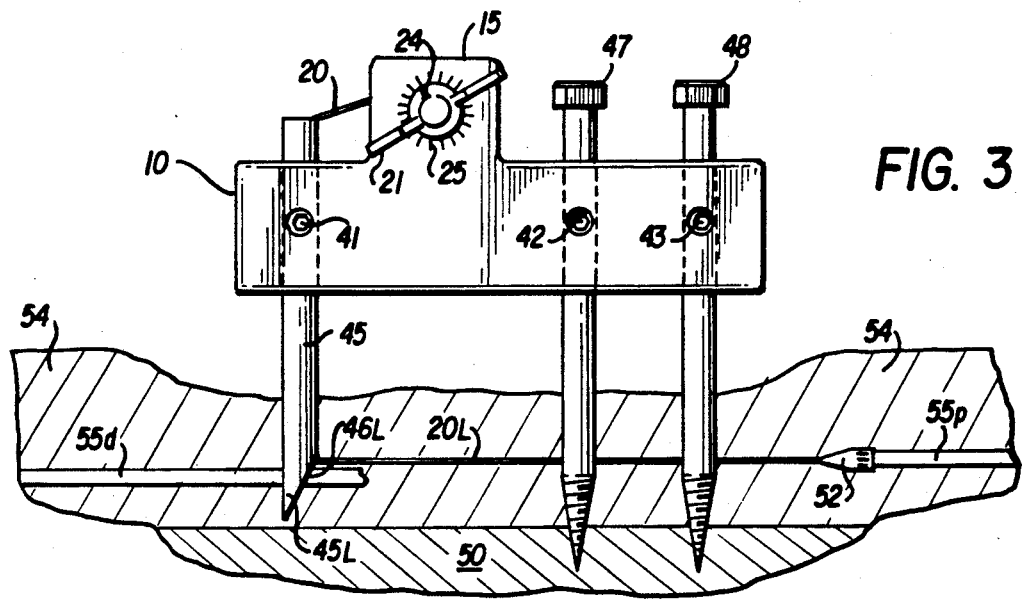
FIG. 3 is a representation of the invention mounted to bone matter, in side elevation view.

The screws, or pins 47 and 48 are long shank pins or screws. When screws are used the screws preferably are constructed with a smooth shank section between the drive head and the screw-thread end. The screw thread end of each screw is preferably a self cutting thread, of the type normally used to drive into bone. The long shaft screws 47 and 48 are passed through the holes 32 and 33 respectively and are screwed into bone matter. This is more clearly shown in FIG. 3. The same components of the invention represented in FIGS. 1, 2 and 3 have been provided with identical call-out numbers, to make cross reference clear. With the screws 47 and 48 screwed into the bone matter 50 as seen in FIG. 3, the block 10 may be secured over the bone matter 50 and/or flesh 54. The set screws 42 and 43 may be screwed in the set screw shaft 37 and 38, respectively so that the set screws impinge on the shaft of the screws 47 and 48, respectively. The set screws will thus be used to hold the block above the work area.

The wire 20 is attached to the drum 16. A hole 17 in the drum is provided to receive an end of the wire and secure the wire so as to guard against slippage of the wire 20 when the drum is rotated. The drum 16 is rotated in the direction indicated by arrow 18 to take up the wire 20. The drum may be rotated manually or a drive motor may be used to rotate the drum. The drum may include a ratchet mechanism (not shown) to hold the rotational position of the drum. The wire 20 is passed through the hollow 46 of the needle 45 and exits at the bottom opening 46L as seen in FIGS. 1 and 3. Attached to the end of the wire is a cone 52. The cone 52 is adopted to receive the end of nerve tissue 55p which is sutured to the cone 52, the sutures passing through the holes in the cone, into the nerve tissue. When the nerve 55p is sutured to the cone, the nerve 55p is effectively attached to the wire 20. When the nerve 55p is attached to the wire 20, the nerve can be lengthened by rotating the drum of the windlass so that the wire is wound around the drum and pulled through the hollow of the needle 45. Since the wire 20 exits from the bottom of the chamber in the hollow needle, the wire section 20L will be pulled into the chamber through the lower opening, at the base of the needle, pulling the cone 52 and the nerve 55p, along the path in which the wire is laid. As the wire 20L and attached cone 52 pull the nerve along the prepared path, the wire and cone are in the process of being extracted from the flesh 54.

It is desirable to move or lengthen nerve tissue very slowly, for example, on the order of 0.5 to 1.0 mm per day. In order to assist the relatively slow advance of the wire and cone by the windlass, an indication 25 is provided on a winged turn key 21 which may be used to manually rotate the drum 16 and take up the wire 20 attached to the drum by the hole 17. Calibrations 25 are provided around the arc followed by the indicator 24 so that accurate advance of the wire and cone may be accomplished thus permitting a great amount of control over the lengthening of nerve tissue.

The member 45 has been described as a hollow tube, hollow shaft or hollow needle that is secured or positively positioned in the block by the set screw. In the preferred embodiment of the invention, as represented in FIGS. 1, 2 and 3, the member 45 is a hollow needle that provides a fixed path with a bottom exit 46L for the wire 20 so that the wire portion 20L may be held in the flesh 54 and create a desirable path for the nerve tissue 65p. The needle 45 also has a sharp end 45L which is used to penetrate the bone and thus secure the lower end of the needle at a fixed location. This fixed location may be used to identify the location of the distal end of the severed nerve tissue 55d.

The location of the screws 47 and 48 and the needle 45 in the block 10, is not deemed to be critical. For example, the screw 48 could be located in the shaft or hole 33 while the screw 47 could be located in the shaft or hole 31. This would leave the shaft or hole 32 available for locating the needle 45. Preferably the needle 45 is located next to the windlass, although such approximate locating is not necessary.

The screws 47 and 48 are used to position or locate the block or bar 10 over the work area while the set screws fix the elevation of the block above the work area.

Alternatively, the block may be mounted or positioned over the working area by other means, if desired. For example, a yoke or frame attached to both the block and the person or animal, receiving the nerve tissue repair work, may be used to secure the block in position. Another mounting vehicle is a cast on the person or animal receiving the nerve tissue repair work.

With the location of the nerve tissue 55d pointed out by the needle 45L and the nerve tissue 55p sutured to the cone 52, the drum 16 of the windlass 12 may be rotated in direction 18 by advancing the winged member 21 in a clockwise direction. When the end of the nerve tissue 55p is sufficiently close to, or overlapping the end of nerve tissue 55d the cone 52 may be separated from the nerve tissue 55p and the proximal end of the nerve tissue may be attached to the distal end of the nerve tissue by suturing, thus physically connecting or rejoining the severed nerve tissue. This puts the nerve tissue in condition for regeneration.

Figure 4:
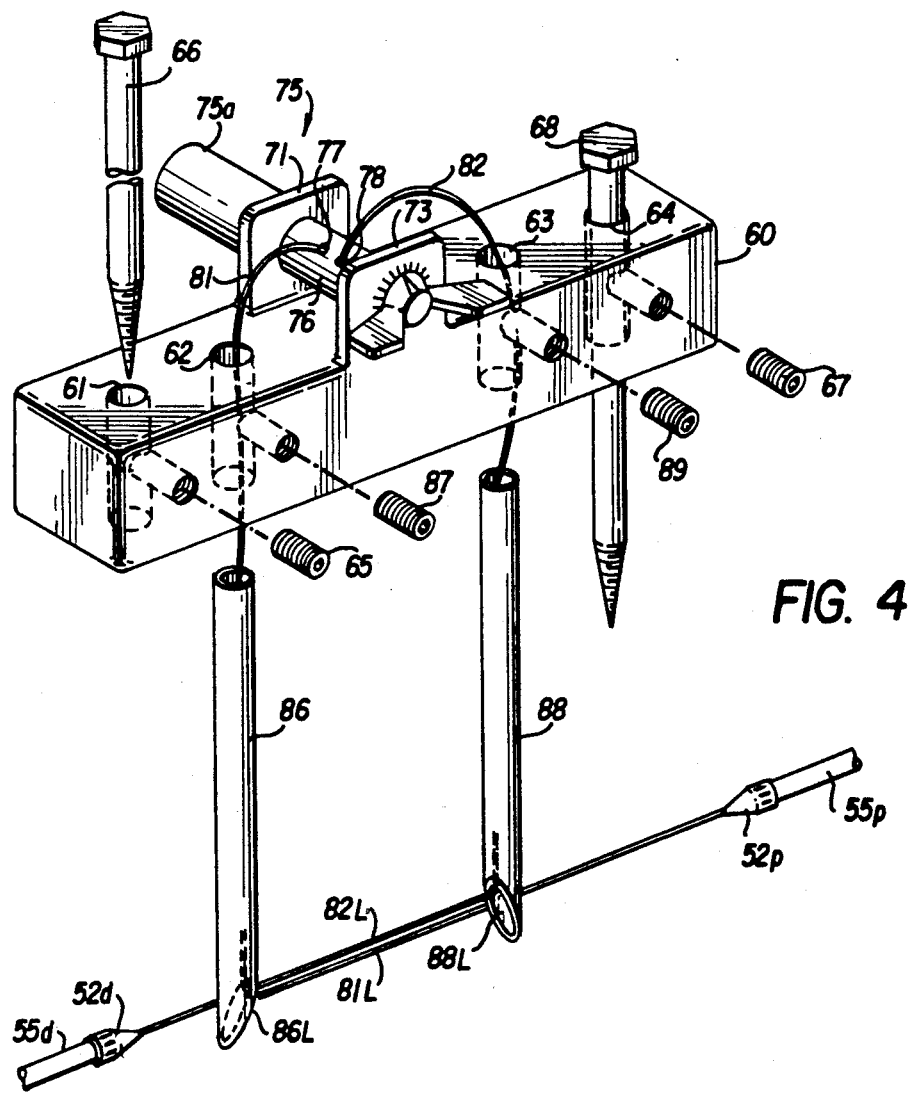
FIG. 4 is a representation of an alternate embodiment of the invention.

FIG. 4 is an alternate construction of the invention, employing the principals of the invention, using a block 60 with four (4) shaft holes 61, 62, 63 and 64. The long shaft bone penetrating screws 66 and 68 may be located in the shaft holes 61 and 64 respectively for locating the block 60 over the work area. The set screws 65 and 67 are used to fix the position of the block 60 above the work area on the screw shafts 66 and 68.

A windlass 75 includes the flanges 71 and 73 which are centrally located on the top surface of the block 60 with the barrel or drum 76 mounted between the flanges 71 and 73. The windlass may be driven by a motor 75a and may also include a ratchet mechanism to prevent unwinding of the wound wire or line. Two (2) wire or line receiving holes 77 and 78 are in the drum to receive wires 81 and 82, respectively. The shaft holes 62 and 63 receive the hollow tubes or needles 86 and 88 respectively and the set screws 87 and 89 are used to fix the depth at which the outlet ports 86L and 88L are positioned below the block 60. One end of the wire 81 is connected to the drum 76 of the windlass via hole 77, the wire passing through the hollow tube 86 and out the lower opening 86L. The other end of wire 81, at 81L is connected to a protective cone 52p in which the stump or end of the nerve tissue 55p is secured. One end of the wire 82 is connected to the drum 76 of the windlass via hole 78, the wire passing through the hollow of tube 88 and out the lower opening 88L. The other end of the wire 82, at 82L is connected to a protective cone 52d in which the end or stump of the nerve tissue 55d is secured.

By rotating the drum 76 of the windlass in, for example, a clockwise direction, the wires 81 and 82 will be uniformly wound on the drum, generating a double come-along, pulling both the nerve tissue ends 55p and 55d together, toward each other.

This apparatus and method has the advantage of lengthening both sections of the severed nerve uniformly and together to an overlapped condition. After the nerve tissue has been lengthened to a maximum accorded by the apparatus, the nerve tissue will be in overlapped condition, that is, overlapped between the shafts 86 and 88 so that the protective cones may be removed from the nerve ends and the nerve ends may be sutured together to promote healing.

Dual paths for the two nerve tissue ends are created by the wires and come-alongs which may be laid in the flesh so as to follow the same path between the lower openings 86L and 88L of the hollow tubes 86 and 88, respectively.

A preferred embodiment of the invention has been shown and described and an alternate embodiment has been shown and described, each with different, suggested structure. Changes and modifications may be made, as will become apparent to those skilled in the art, without departing from the invention as defined in the claims.

What is claimed is:

1. Apparatus for lengthening nerve tissue in a body, said apparatus comprising:
   a) means for mounting a windlass over a body in the approximate area of a nerve tissue to be lengthened and, a windlass mounted on said means for mounting;
   b) means for providing a first path and a second path, said first path extending substantially from said windlass into said body, said second path in said body and defining a path along which said nerve tissue is to be extended, said first path connected to said second path;
   c) line means having a first end and connected at said first end to said windlass, said line means extending along said first path and along said second path at least to said nerve tissue; and,
   d) means for connecting said nerve tissue to a second end of said line means for pulling said nerve tissue along said second path.

2. Apparatus as in claim 1 and in which said means for mounting said windlass over said body includes a block having a first flange and a second flange and said windlass includes a drum mounted for rotational movement between said first flange and said second flange.

3. Apparatus as in claim 2 and in which said block includes a first shaft opening and said apparatus further includes a first screw member adapted to enter said first shaft opening and extend therefrom and be screwed into a bone matter of said body.

4. Apparatus as in claim 3 and said block further includes a set screw opening communicating with said first shaft opening, said set screw opening adapted to receive a set screw for fixing said block to said first screw member for locating said block over said body.

5. Apparatus as in claim 2 and in which said first end of said line means is connected to said drum for being wound around said drum in response to rotational movement of said drum.

6. Apparatus as in claim 5 and in which said windlass includes a means for rotating said drum for winding said line means on said drum for drawing said line means along said second path toward said first path.

7. Apparatus as in claim 2 and in which said line means is a wire and said first end of said wire is connected to said drum for winding said wire around said drum in response to rotational movement of said drum.

8. Apparatus as in claim 2 and in which said windlass further includes a means for rotating said drum.

9. Apparatus as in claim 8 and in which said means for rotating said drum includes a ratchet means for holding said drum against backward rotation.

10. Apparatus as in claim 8 and in which said means for rotating said drum is a motor.

11. Apparatus as in claim 2 and in which said first path is a hollow needle extending from said block.

12. Apparatus as in claim 2 and in which said first path is a hollow tube and said hollow tube extends from said block.

13. Apparatus as in claim 1 and in which said line means is a cable.

14. Apparatus as in claim 1 and in which said line means is a plastic line.

15. Apparatus as in claim 1 and in which said line means is a stainless steel wire.

16. Apparatus as in claim 1 and in which said first path is a hollow needle.

17. Apparatus as in claim 1 and in which said first path is a hollow tube.

18. A method for lengthening a nerve tissue in a body comprising the steps of:
   a) mounting a windlass, in fixed position, in the approximate area of a nerve to be lengthened;
   b) making a first path from said windlass said body, said first path connecting to a second path in said body along which said nerve tissue is to be drawn;
   c) connecting a first end of a line to a rotatable drum of said windlass, extending said line through said first path and along said second path and connecting a second end of said line to said nerve tissue; and,
   d) rotating said drum for winding said line around said drum for drawing said line through said first path and through said second path for pulling said nerve tissue along said second path for lengthening said nerve tissue.

* * * * *